(12) United States Patent
Yokota

(10) Patent No.: US 11,273,291 B2
(45) Date of Patent: Mar. 15, 2022

(54) CATHETER ASSEMBLY

(71) Applicant: TERUMO KABUSHIKI KAISHA, Tokyo (JP)

(72) Inventor: Takayuki Yokota, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 577 days.

(21) Appl. No.: 16/256,861

(22) Filed: Jan. 24, 2019

(65) Prior Publication Data

US 2019/0151621 A1 May 23, 2019

Related U.S. Application Data

(63) Continuation of application No. PCT/JP2017/028309, filed on Aug. 3, 2017.

(30) Foreign Application Priority Data

Aug. 4, 2016 (JP) .............................. JP2016-153598

(51) Int. Cl.
*A61M 25/06* (2006.01)
*A61M 5/158* (2006.01)
*A61M 25/01* (2006.01)

(52) U.S. Cl.
CPC ...... *A61M 25/0631* (2013.01); *A61M 25/065* (2013.01); *A61M 25/0662* (2013.01);
(Continued)

(58) Field of Classification Search
CPC ............ A61M 25/0631; A61M 25/065; A61M 25/0662; A61M 5/158; A61M 2025/0656;
(Continued)

(56) References Cited

U.S. PATENT DOCUMENTS

2001/0041875 A1* 11/2001 Higuchi ................ A61M 25/06
604/272
2009/0105651 A1* 4/2009 Wada .................... A61M 25/06
604/164.01

FOREIGN PATENT DOCUMENTS

CN 1655840 A 8/2005
CN 1738658 A 2/2006
(Continued)

OTHER PUBLICATIONS

International Searching Authority, "International Search Report," issued in connection with International Patent Application No. PCT/JP2017/028309, dated Oct. 10, 2017.
(Continued)

*Primary Examiner* — Lauren P Farrar
(74) *Attorney, Agent, or Firm* — Foley & Lardner LLP

(57) ABSTRACT

A catheter assembly includes: a catheter having an inner cavity extending along a center axis of the catheter, the catheter comprising, on a distal side, a tapered portion that is tapered in a distal direction; and an inner needle retractably located in the inner cavity. The inner needle comprises, on a distal side, a blade surface that is inclined with respect to a center axis of the inner needle. The tapered portion covers a proximal end portion of the blade surface in an assembled state in which the inner needle is located in the inner cavity, and an inner shape of a distal-most end of the tapered portion conforms to the blade surface.

18 Claims, 10 Drawing Sheets

(52) U.S. Cl.
CPC ......... *A61M 5/158* (2013.01); *A61M 25/0105* (2013.01); *A61M 2025/0656* (2013.01); *A61M 2025/0681* (2013.01); *A61M 2025/0687* (2013.01)

(58) Field of Classification Search
CPC ...... A61M 2025/0687; A61M 25/0105; A61M 2025/0681
See application file for complete search history.

(56) References Cited

FOREIGN PATENT DOCUMENTS

| CN | 200973906 Y | 11/2007 |
|---|---|---|
| CN | 101098728 A | 1/2008 |
| CN | 101316621 A | 12/2008 |
| CN | 201283135 Y | 8/2009 |
| DE | 10 2006 013 096 A1 | 9/2007 |
| EP | 0 615 768 A2 | 9/1994 |
| JP | S60-122152 U | 8/1985 |
| JP | H10-235 A | 1/1998 |
| TW | 201424787 A | 7/2014 |
| WO | WO-93/10849 A1 | 6/1993 |
| WO | WO-99-16486 A1 | 4/1999 |

OTHER PUBLICATIONS

International Searching Authority, "Written Opinion," issued in connection with International Patent Application No. PCT/JP2017/028309, dated Oct. 10, 2017.
Translation of the Written Opinion of the International Searching Authority dated Oct. 10, 2017 in corresponding application No. PCT/JP2017/028309.
Office Action dated Oct. 21, 2020 in corresponding Chinese Patent Application No. 201780047117.7.

* cited by examiner

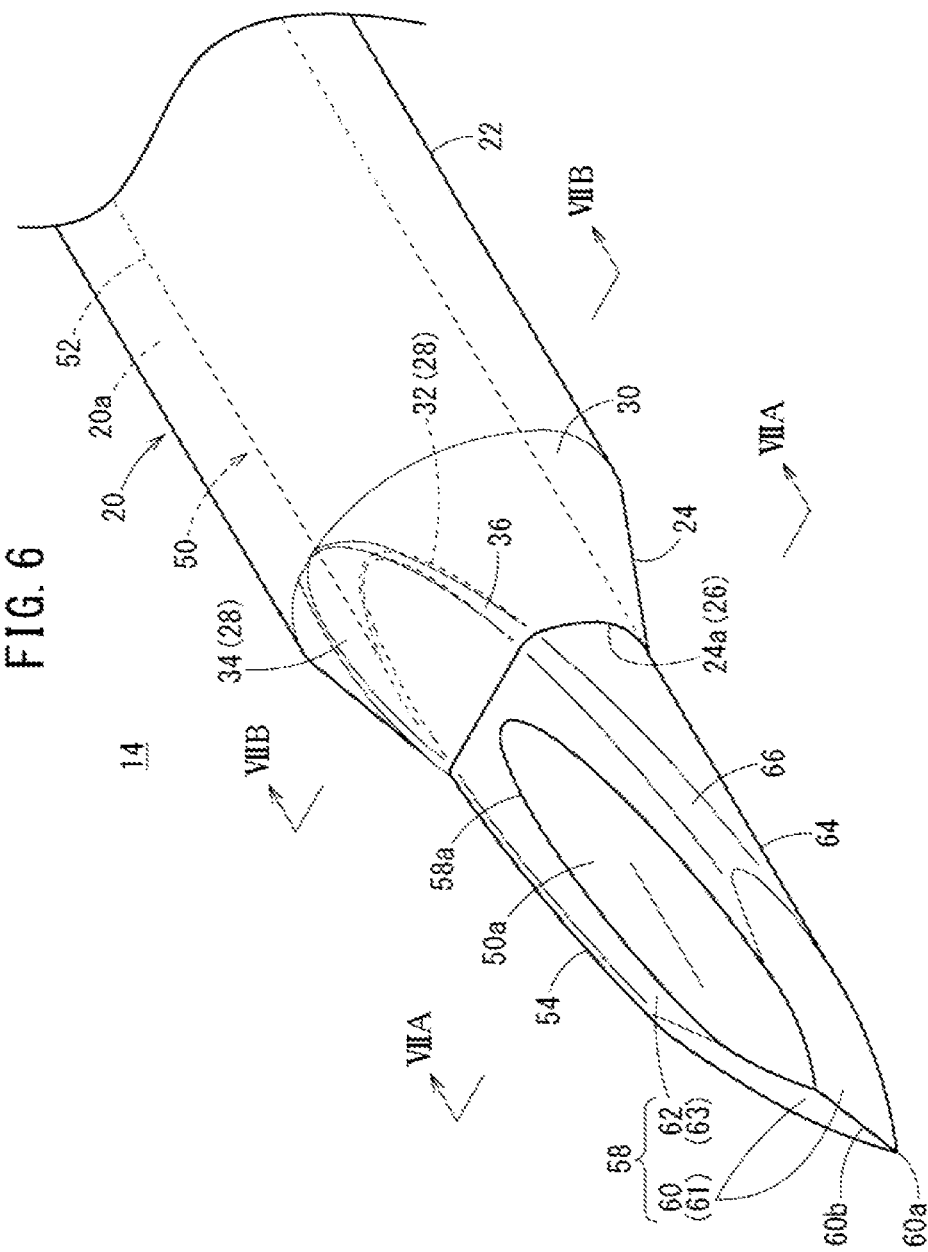

CATHETER ASSEMBLY

CROSS-REFERENCE TO RELATED APPLICATIONS

This is a bypass continuation of PCT Application No. PCT/JP2017/028309, filed on Aug. 3, 2017, which claims priority to Japanese Application No. 2016-153598, filed on Aug. 4, 2016. The contents of these applications are hereby incorporated by reference in their entireties.

BACKGROUND

The present disclosure relates to a catheter assembly including a multiple structure needle having an inner needle inserted through a catheter, the inner needle being exposed from a distal end of the catheter.

A catheter assembly is used in construction of an introduction part of an infusion line in a patient at infusion. JP 10-235 A discloses a catheter assembly having a double structure needle with a structure in which an inner needle is inserted through a catheter with a needle tip exposed from the distal end of the catheter. In use of the catheter assembly, a user punctures a patient's body with a double structure needle and advances the catheter into the blood vessel, and thereafter extracts the inner needle from the catheter to hold the catheter in place.

Here, in a case in which a proximal end of a blade surface of the inner needle is separated away from the distal end of the catheter, the user tends to focus on insertion of the catheter and tends to perform deep puncture with the needle. Deep puncture with the needle in this manner might lead to a possibility that the needle tip of the inner needle pierces into a blood vessel inner wall, making it difficult to perform insertion of the catheter in some cases. For this reason, for example, the catheter assembly (injection needle) disclosed in JP 10-235 A has a configuration in which the catheter covers the blade surface of the inner needle (inner needle cutting portion) in an assembled state where the inner needle is inserted through the catheter.

SUMMARY

The blade surface, however, is normally formed as a flat surface inclined at a predetermined angle with respect to a center axis of the inner needle, and the catheter assembly disclosed in JP 10-235 A forms a step between a tapered distal end of the catheter and the blade surface in an assembled state (refer to FIG. 1 in JP 10-235 A). Presence of this type of step would cause a great resistance to be applied to the step from the living body during puncture, making it difficult to insert the catheter into the blood vessel.

Certain embodiments described in the present disclosure have been developed in view of the above circumstances, and aims to provide a catheter assembly capable of reducing the amount of protrusion of the inner needle from the catheter and reducing the resistance applied on the catheter at the time of puncture, enabling satisfactory insertion of the catheter into the living body.

According to one embodiment, a catheter assembly includes: a catheter having an inner cavity along a center axis and having, on a distal side, a tapered portion tapered in a distal direction; and an inner needle retractably inserted through the inner cavity, wherein the inner needle on a distal side, a blade surface including inclined with respect to the center axis of the inner needle, the tapered portion covers a proximal end portion of the blade surface in an assembled state where the inner needle is inserted through the inner cavity, and an inner shape of distal-most end of the tapered portion conforms to the blade surface.

According to the above embodiment, the catheter assembly enables satisfactory insertion of a catheter into a living body by a multiple structure needle with an inner needle inserted through the catheter. That is, a multiple structure needle has a configuration in which the tapered portion covering the proximal end portion of the blade surface reduces the amount of protrusion of the inner needle protruding from the distal-most end of the catheter, making it possible to suppress an influence (damage, or the like) of the inner needle on blood vessel inner walls at the time of puncture. In addition, the catheter assembly has a configuration in which an inner shape of distal-most end of the tapered portion conforms to the blade surface, thereby formation of a step between the blade surface and the catheter is suppressed, leading to reduction of resistance applied to the catheter when the catheter enters a living tissue. This enables a user to insert the catheter smoothly into the living body.

In one aspect, the distal-most end of the tapered portion is in contact with an outer peripheral surface of the inner needle including the blade surface.

With the distal-most end of the tapered portion being in contact with the outer peripheral surface of the inner needle, it is possible to further reliably suppress formation of the step between the catheter and the blade surface. This makes it possible to insert the catheter more satisfactorily.

In one aspect, the tapered portion includes: an opposing surface opposing the blade surface among inner surfaces forming the inner cavity; and an outer flat surface formed in a flat shape on an outer surface side that corresponds to a circumferential position of the opposing surface.

In this manner, the tapered portion having the outer flat surface makes it possible to form an outer shape of the double structure needle (catheter) that matches the blade surface. With this configuration, it is possible to achieve a smooth transition from the blade surface to the tapered portion when the catheter is inserted into the living body.

In one aspect, an inclination angle of the outer flat surface with respect to the blade surface is smaller than an inclination angle of a proximal side portion of the blade surface with respect to the center axis of the inner needle.

With the inclination angle of the outer flat surface with respect to the blade surface formed to be smaller than an inclination angle of the proximal side portion of the blade surface, it is possible to sufficiently widen an obtuse angle of a boundary portion between the blade surface and the outer flat surface. Accordingly, it is possible to achieve further smooth transition from the blade surface to the tapered portion when the catheter is inserted into the living body.

In one aspect, an outer peripheral surface of the distal side of the inner needle in a cross section orthogonal to the center axis of the inner needle includes the blade surface, an arcuate surface, and a rounded corner surface joining the blade surface with the arcuate surface, the rounded corner having a larger curvature than the arcuate surface; and the tapered portion in a cross section orthogonal to the center axis of the catheter in the assembled state includes a flat portion having the opposing surface, an arcuate portion opposing the arcuate surface, and a rounded corner portion joining the flat portion with the arcuate portion, the rounded corner portion opposing the rounded corner surface.

With the presence of the rounded corner surface on the inner needle in this manner, it is possible to suppress formation of a step between the catheter and the blade surface even in a case in which the tapered portion of the catheter is not previously shaped (that is, even with a conical shape).

In one aspect, the flat portion, the arcuate portion and the rounded corner portion are preliminarily shaped in a state where the inner needle is not inserted through the inner cavity.

With the flat portion, the arcuate portion, and the rounded corner portion of the catheter assembly being preliminarily shaped, it is possible to suppress the misalignment between the catheter and the inner needle in the assembled state and more reliably suppress formation of the step.

In one aspect, the inner needle has a needle hole at the center axis, the blade surface includes a needle tip opening communicating with the needle hole, and the tapered portion covers a proximal end portion of the needle tip opening.

With the tapered portion covering the proximal end portion of the needle tip opening in this manner, it is possible to suppress occurrence of damage in the living tissue caused by a lip of the proximal end portion of the needle tip opening.

In one aspect, the blade surface including a first area having a distal end capable of forming a cut; and a second area continuous with a proximal end of the first area, the second area being formed with a surface different from the first area and configured to widen the cut; and the tapered portion partially covers the second area without covering the first area in the assembled state.

With the blade surface including the first area and the second area in this manner, it is possible to easily form a cut using the first area and widen the cut using the second area. Because the tapered portion partially covers the second area without covering the first area, it is possible to reduce the amount of protrusion of the inner needle without lowering puncture capability that can be obtained by the first area.

In one aspect, the catheter is formed of a material containing polyurethane.

With the catheter formed of a material containing polyurethane in this manner, it is possible, in manufacturing the catheter, to adopt a manufacturing method in which the catheter is processed into a desired shape with a method of pressing the catheter against a heated mold or the like. Thereafter, the catheter may be covered with a tubular material and heated to be formed into a shape that conforms to a shape of the inner needle or the blade surface of the inner needle. This manufacturing method causes heat shrinkage in the catheter by heating, making it possible to allow the tapered portion to further correspond to the shape of the blade surface and mold the catheter into a shape with substantially no step between the tapered distal end of the catheter and the blade surface.

According to the present invention, the catheter assembly is capable of reducing the amount of protrusion of the inner needle from the catheter and reducing the resistance applied on the catheter during puncture, enabling satisfactory insertion of the catheter into the living body.

BRIEF DESCRIPTION OF THE DRAWINGS

FIG. 6 is an enlarged perspective view illustrating a distal side of a double structure needle according to a first modification.

DETAILED DESCRIPTION

Hereinafter, embodiments of a catheter assembly according to the present invention will be described in detail with reference to the accompanying drawings.

A catheter assembly according to certain embodiments is used for forming an introduction part of an infusion agent or a blood transfusion agent at the time of performing infusion, transfusion, or the like on a patient (living body). Examples of the catheter assembly include a peripheral venous catheter, a peripheral arterial catheter, a central venous catheter, a PICC, and a midline catheter. The configurations of the embodiments described herein are not limited to the catheters described above and can be applied to various devices (for example, syringes) for incising a living tissue with an inner needle and inserting a catheter to the internal portion of the living tissue.

Figure 1:
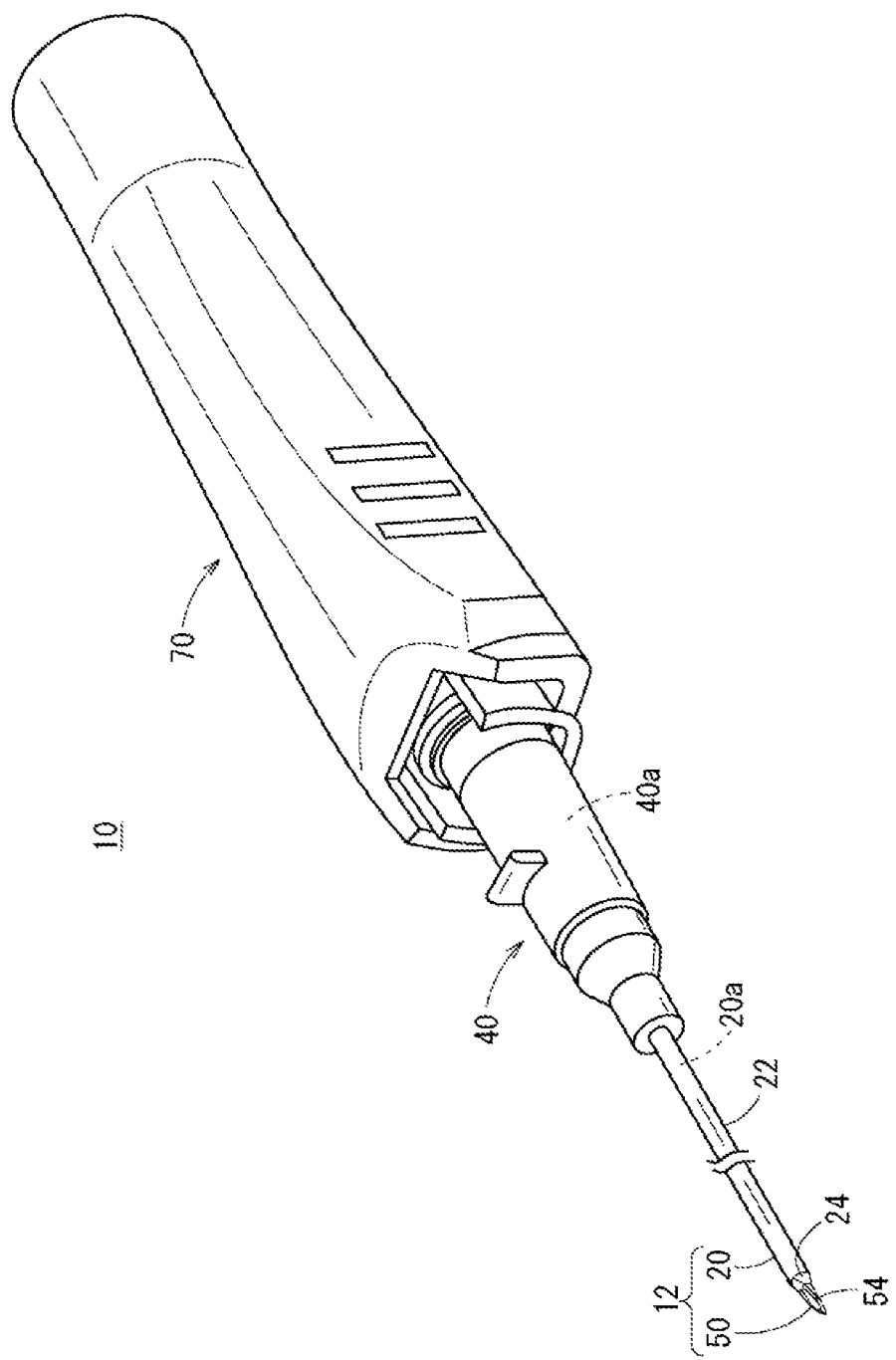
FIG. 1 is a perspective view illustrating an entire configuration of a catheter assembly according to an embodiment of the present invention.

As illustrated in FIG. 1, a catheter assembly 10 according to one embodiment of the present invention includes a catheter 20, a catheter hub 40 for fixedly holding the catheter 20, an inner needle 50, a needle hub 70 for fixedly holding the inner needle 50. Then, the catheter assembly 10 includes a double structure needle 12 having the catheter 20 overlapped with the inner needle 50 (inner needle 50 is inserted through the catheter 20) in an assembled state. Note that the needle of the catheter assembly 10 may have a multiple structure in which three or more members (for example, the catheter 20, the inner needle 50, and a guide wire (not illustrated)) are overlapped in order from the outer side.

In use of the catheter assembly 10, a vein of a patient is punctured with the double structure needle 12 and the catheter 20 is inserted intravenously, and thereafter, the inner needle 50 is pulled out from the catheter 20. This allows the catheter 20 to be inserted intravenously, while allowing the proximal side of the catheter 20 and the catheter hub 40 to be exposed on the patient's skin. Subsequently, an infusion tube (not illustrated) is connected to the proximal end of the catheter hub 40, making it possible to supply an infusion agent or the like to the patient via this infusion tube.

The catheter 20 is a tubular body having appropriate levels of flexibility, and constitutes an outer needle in the above-described double structure needle 12. The interior of the catheter 20 includes an inner cavity 20a extending along the center axis of the catheter 20 and penetrating the distal end and the proximal end of the catheter 20. The inner cavity 20a is formed to have a diameter capable of accommodating the inner needle 50 and capable of flowing an infusion agent or the like.

The catheter 20 includes: an outer needle side barrel 22 formed long in an axial direction and constituting a major part of the catheter 20; and a tapered portion 24 protruding short in a distal direction from a distal end of the outer needle side barrel 22.

The outer needle side barrel 22 extends in the axial direction with a constant outer diameter. The inner cavity 20a of the outer needle side barrel 22 is formed to be slightly larger than the outer diameter of the inner needle 50. The proximal end portion of the outer needle side barrel 22 is fixed to the distal end portion inside the catheter hub 40 using an appropriate fixing method such as fusion bonding, adhesion, and caulking. In addition, a proximal end opening (not illustrated) communicating with the inner cavity 20a is provided at the proximal end of the outer needle side barrel 22. The length of the outer needle side barrel 22 may be designed in accordance with the application and various conditions, so as to be set to about 14 mm to 500 mm, or set to about 14 mm to 400 mm, or set to about 14 mm to 200 mm, for example.

Figure 2:
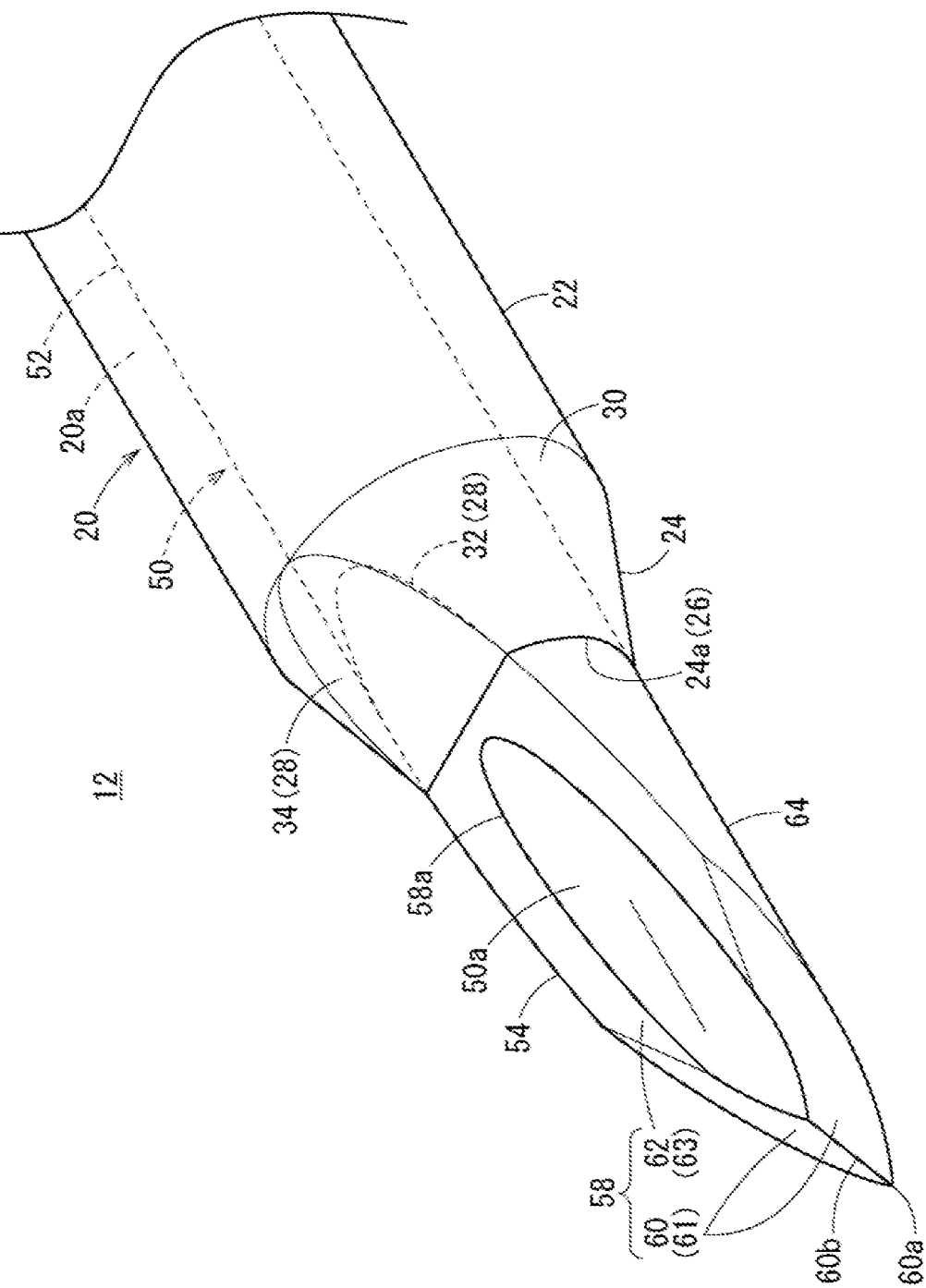
FIG. 2 is an enlarged perspective view illustrating a distal side of a double structure needle of FIG. 1.

As illustrated in FIG. 2, the tapered portion 24 has a tapered shape having outer diameter gradually decreasing from the proximal end connected to the outer needle side barrel 22 in the distal direction. At the distal-most end 24a of the tapered portion 24 (catheter 20), a distal end opening 26 communicating with the inner cavity 20a is provided. The configuration of the tapered portion 24 also relates to the shape of the inner needle 50, and thus will be described below in detail.

The material to form the catheter 20 is not particularly limited, and soft resin material is suitable. Examples include: fluoride resin such as polytetrafluoroethylene (PTFE), ethylene tetrafluoroethylene copolymer (ETFE), and perfluoroalkoxy fluororesin (PFA); an olefinic resin such as polyethylene and polypropylene or a mixture thereof; and a polyurethane, a polyester, a polyamide, a polyether nylon resin, a mixture of an olefinic resin and an ethylene/vinyl acetate copolymer. The catheter 20 according to the present embodiment is formed of polyurethane having heat shrinkability.

Returning to FIG. 1, the catheter hub 40 is formed in a cylindrical shape that is harder and larger in diameter than the catheter 20 and long in the axial direction. A hollow portion 40a communicating with the proximal end opening of the outer needle side barrel 22 is provided inside the catheter hub 40. Although not illustrated, the hollow portion 40a may house a hemostatic valve for preventing back flow of blood at the time of puncture with the inner needle 50, a plug for penetrating the hemostatic valve in accordance with insertion of the infusion tube to allow infusion, or the like.

The material to form the catheter hub 40 is not particularly limited, and examples of these include a thermoplastic resin such as polypropylene, polycarbonate, polyamide, polysulfone, polyallylate, and methacrylate-butylene-styrene copolymer.

Meanwhile, the inner needle 50 is a hollow tube having a rigidity capable of puncturing the skin of the living body, and is disposed to penetrate through the inner cavity 20a of the catheter 20 and the hollow portion 40a of the catheter hub 40, in the assembled state illustrated in FIG. 1. The inner needle 50 includes: an inner needle side barrel 52 longer than the entire length of the catheter 20; and a needle tip portion 54 connected to the distal end of the inner needle side barrel 52 and protruding short in the distal direction. A needle hole 50a is linearly formed to penetrate through the center axis portion of the inner needle side barrel 52 and the needle tip portion 54.

The inner needle side barrel 52 of the inner needle 50 is a site extending in a tubular shape in the axial direction of the inner needle 50 and extends with a constant outer diameter and inner diameter along the center axis of the inner needle 50. The proximal end portion of the inner needle side barrel 52 is firmly fixed inside the needle hub 70 with an appropriate fixing method such as fusion bonding, adhesion, and insert molding.

As illustrated in FIG. 2, a tubular body manufactured to have a same diameter as the inner needle side barrel 52 is appropriately cut into the needle tip portion 54 of the inner needle 50 to have the blade surface 58 at a portion in the circumferential direction at the time of manufacture. This blade surface 58 includes a needle tip opening 58a communicating with the needle hole 50a. The length in the axial direction of the needle tip portion 54 may preferably be 1 mm to 10 mm, for example, depending on the entire length and the outer diameter of the inner needle 50.

Furthermore, the blade surface 58 includes three surfaces (a pair of distal end split surfaces 60 and a proximal end inclined surface 62). The pair of distal end split surfaces 60 are continuous with a point 60a and a ridge portion 60b at distal-most end so as to constitute a first area 61 that goes around the needle tip opening 58a to be separated away from each other in the proximal side. The proximal end inclined surface 62 is continuous with the proximal end of the pair of distal end split surfaces 60 and constitutes a second area 63 that goes around the needle tip opening 58a in the proximal direction. In the present embodiment, a width of the first area 61 gradually increases in the proximal direction, while a width of an edge portion (edge) of the second area 63 gradually decreases in the proximal direction. The pair of distal end split surfaces 60 and the proximal end inclined surface 62 can be formed by cutting the tubular body three times. Note that the shape of the blade surface 58 is not particularly limited, and may be an oval shape by diagonally cutting the tubular body once.

Figure 3:
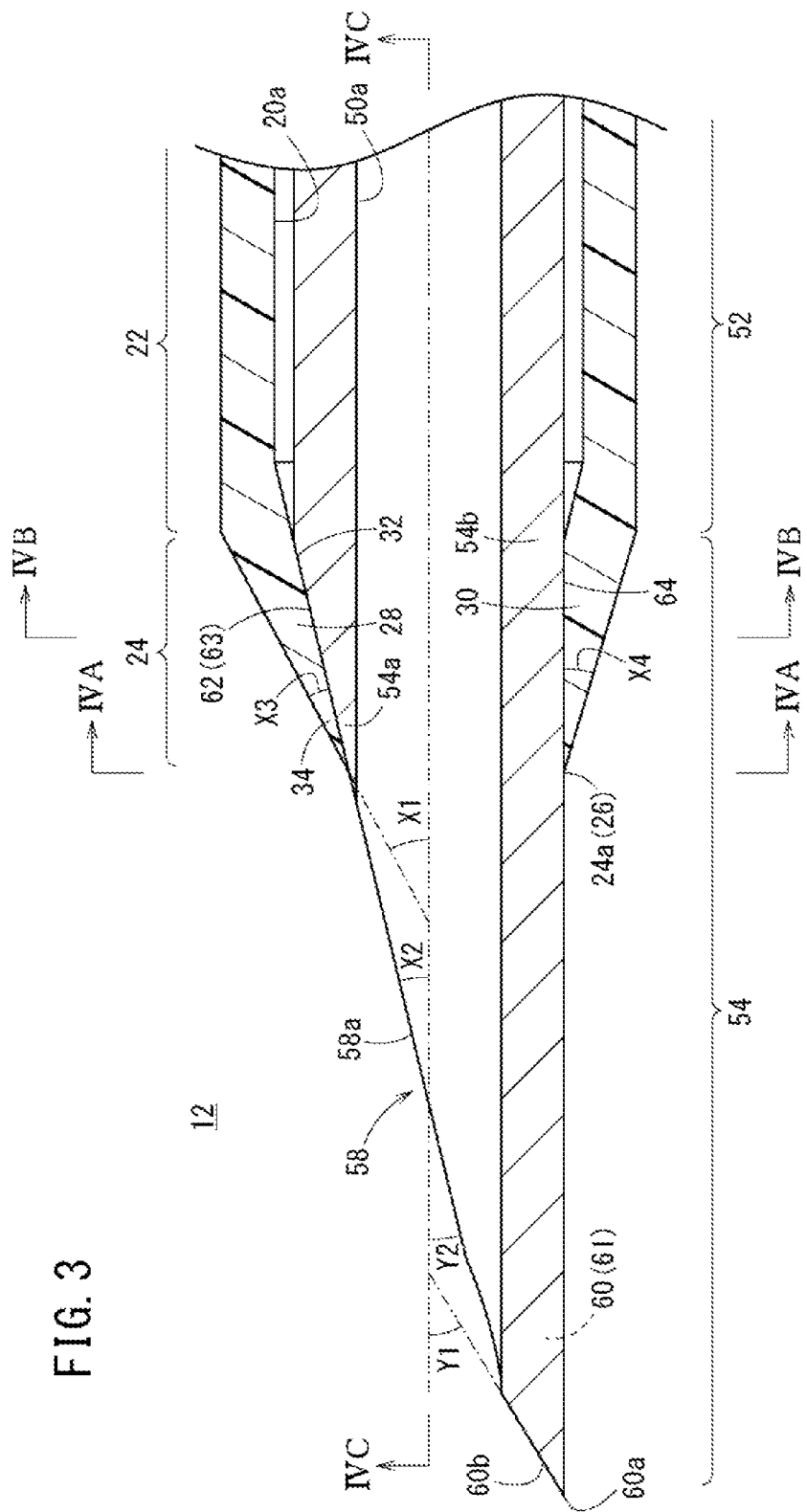
FIG. 3 is a side cross section of the double structure needle of FIG. 2.

The pair of distal end split surfaces 60 (first area 61) are formed in a flat shape, each of which faces outward in a width direction opposite to each other, and is formed to be short in the axial direction in a side cross section in FIG. 3. This pair of distal end split surfaces 60, together with the point 60a and the ridge portion 60b (boundary line), constitutes a portion that forms a cut in the living tissue. An inclination angle Y1 of the ridge portion 60b with respect to the center axis of the inner needle 50 is preferably designed to be an angle facilitating insertion of the first area 61, for example, preferably in a range of 15° to 40°.

In contrast, the proximal end inclined surface 62 (second area 63) is formed to be longer than the first area 61 in the axial direction corresponding to the inner diameter of the needle tip opening 58a and the thickness of the wall portion of the tubular body in the side cross section illustrated in FIG. 3. The proximal end inclined surface 62 has a flat shape that faces upward and the distal direction. An inclination angle Y2 of the proximal end inclined surface 62 (proximal side portion of the blade surface 58) with respect to the center axis of the inner needle 50 is designed to be the inclination angle Y1 or less (0°<Y2≤Y1) of the ridge portion 60b. The inclination angle Y2 of the proximal end inclined surface 62 is preferably designed to be an angle capable of gently widening the cut, for example, preferably in a range of 5° to 20°.

A formation position of the proximal end inclined surface 62 on more toward the proximal side than the needle tip opening 58a on the needle tip portion 54 has a substantially D shape in a cross section (refer to FIGS. 4A and 4B) orthogonal to the center axis of the inner needle 50. More specifically, the needle tip portion 54 includes: an inclined wall portion 54a obtained by linearly cutting the upper portion in the width direction; and an arcuate wall portion 54b going around in an arcuate shape from both side edges in the width direction of the inclined wall portion 54a. As the proximal end inclined surface 62 on the outer peripheral surface side of the inclined wall portion 54a is inclined, the wall thickness gradually increases in the proximal direction in a side cross section illustrated in FIG. 3. Because the arcuate surface 64 on the outer peripheral side of the arcuate wall portion 54b is constant, the wall thickness is also constant in the proximal direction in side cross section.

The material to form the inner needle 50 is not particularly limited, and examples include metal materials such as stainless steel, aluminum or aluminum alloy, titanium or titanium alloy, hard resin, and ceramics. Note that the inner needle 50 may include a groove portion obtained by partially cutting the outer peripheral surface in the axial direction, or may include a lateral hole communicating with the needle hole 50a. In addition, the inner needle 50 may be a solid needle.

Returning to FIG. 1, the needle hub 70 is formed as a case by which the double structure needle 12 is operable on the proximal side, and fixedly holds the inner needle 50 inside this case. The needle hub 70 is formed in an elongated shape easily grasped with one hand while accommodating and connecting with the proximal side of the catheter hub 40. Configurations of the catheter hub 40 and the needle hub 70 of the catheter assembly 10 are not limited to the above-described configuration, and various configurations may be adopted.

Next, the double structure needle 12 in a state (assembled state) where the above configuration is assembled to enable puncture of a patient will be described in detail. As described above, the catheter assembly 10 inserts the inner needle 50 through the inner cavity 20a of the catheter 20, with center axis of the catheter 20 and the inner needle 50 coaxially arranged in the assembled state. The needle tip portion 54 at the distal end of the inner needle 50 is exposed from the distal end (distal-most end 24a) of the catheter 20.

Here, in the present embodiment, as illustrated in FIGS. 2 and 3, the tapered portion 24 of the catheter 20 partially covers the proximal side of the blade surface 58 (proximal end inclined surface 62) of the inner needle 50 in order to reduce the amount of protrusion of the inner needle 50 protruding from the distal end of the catheter 20. Furthermore, in order to suppress formation of the step with the proximal end inclined surface 62, the inner shape of the distal-most end 24a of the tapered portion 24 is configured to be along the proximal end inclined surface 62 of the needle tip portion 54 in the assembled state.

Figure 4A:
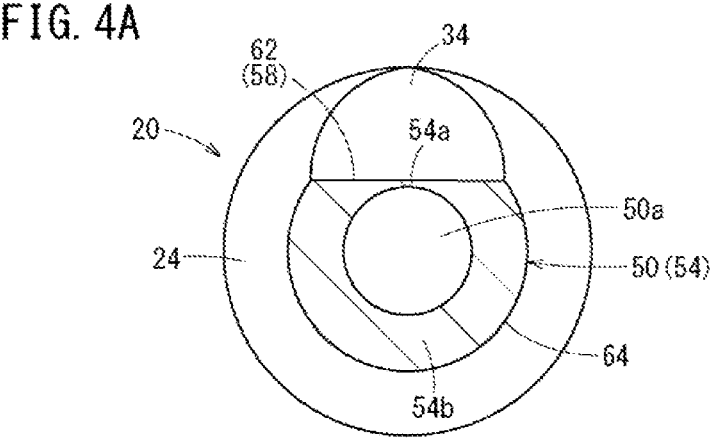
FIG. 4A is a cross section taken along line IVA-IVA of FIG. 3.
Figure 4B:
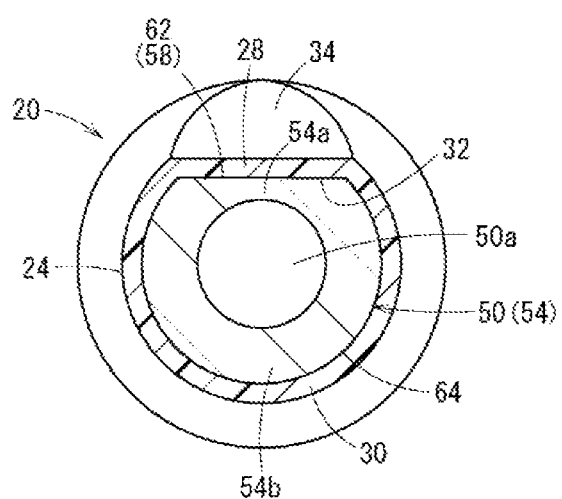
FIG. 4B is a cross section taken along line IVB-IVB of FIG. 3.

Specifically, the tapered portion 24 includes a flat portion 28 at a position in phase with the inclined wall portion 54a and includes an arcuate portion 30 at a position in phase with the arcuate wall portion 54b among positions in the circumferential direction surrounding the needle tip portion 54, in a cross section orthogonal to the center axis of the inner needle 50 (refer to FIGS. 4A and 4B). The thickness of the catheter 20 gradually increases in the proximal direction at the flat portion 28 and the arcuate portion 30 so as to be constant at the outer needle side barrel 22.

The flat portion 28 includes: an opposing surface 32 constituting a portion of an inner surface of the inner cavity 20a and opposing the blade surface 58; and an outer flat surface 34 constituting the outer peripheral surface of the catheter 20 and located on a side opposite the opposing surface 32 (position in phase with the position in the circumferential direction). The opposing surface 32 is formed in a shape that corresponds to an outer shape of the proximal end inclined surface 62 of the inner needle 50.

Figure 4C:
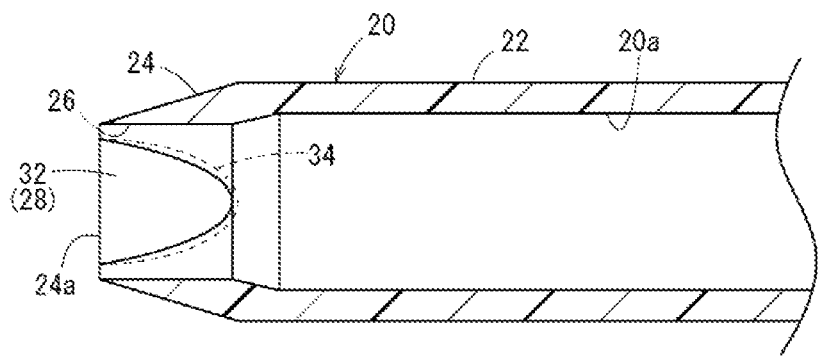
FIG. 4C is a cross section taken along line IVC-IVC of FIG. 3.

That is, as illustrated in FIGS. 3 and 4C, the opposing surface 32 is formed in a semielliptical shape substantially the same as a semielliptical shape of the proximal end inclined surface 62, and an inclination angle X2 with respect to the center axis of the catheter 20 corresponds to the inclination angle Y2 of the proximal end inclined surface 62. With this configuration, the opposing surface 32 is brought into a state of surface contact with the proximal end inclined surface 62 from the distal-most end 24a in the assembled state. The opposing surface 32 and the outer flat surface 34 intersect with each other at an acute angle at the distal-most end 24a of the tapered portion 24, with the distal-most end 24a of the tapered portion 24 being in line contact with the proximal end inclined surface 62 in the width direction.

The outer flat surface 34 is formed in a semielliptical shape substantially the same as the semielliptical shape of the opposing surface 32. This allows the outer peripheral surface of the tapered portion 24 as a whole to have a substantially conical shape, with a formation portion of the outer flat surface 34 alone being inclined in a shape corresponding to the proximal end inclined surface 62 of the inner needle 50 being covered.

The inclination angle X1 of the outer flat surface 34 with respect to the center axis of the catheter 20 is preferably set to be somewhat greater than the inclination angle X2 of the opposing surface 32. The inclination angle X2 of the opposing surface 32 corresponds to the inclination angle Y2 of the proximal end inclined surface 62. As a result, an intersecting angle X3 (=X1−X2: inclination angle of the outer flat surface 34 with respect to the proximal end inclined surface 62) between the opposing surface 32 and the outer flat surface 34 is set to be smaller than the inclination angle Y2 of the proximal end inclined surface 62, leading to an angle between the outer flat surface 34 and the blade surface 58 (proximal end inclined surface 62) being an obtuse angle to a sufficient degree. Note that the intersecting angle X3 between the opposing surface 32 and the outer flat surface 34 may be set greater than the inclination angle Y2 or may be set to be equal to the inclination angle Y2 depending on the strength and length required for the tapered portion 24.

Meanwhile, the inner surface of the arcuate portion 30 is formed in the same curvature as the arcuate surface 64 of the needle tip portion 54, so as to be in surface contact with the arcuate surface 64 in the circumferential direction. The inner surface of the arcuate portion 30 extends in parallel in the axial direction of the catheter 20. An inclination angle X4 of the outer peripheral surface of the arcuate portion 30 with respect to the center axis (inner surface) of the catheter 20 is greater than the intersecting angle X3 of the flat portion 28.

Furthermore, the flat portion 28 provided in the tapered portion 24 is preliminarily shaped in a state where the inner needle 50 is not inserted through the inner cavity 20a. The blade surface 58 of the inner needle 50 and the opposing surface 32 of the catheter 20 are aligned in phase at the time of assembly, thereby presenting the double structure needle 12 illustrated in FIGS. 1 to 4B. The opposing surface 32 of the catheter 20 is capable of guiding the blade surface 58 of the inner needle 50 when the inner needle 50 is inserted from the proximal side of the catheter 20, enabling suppression of protrusion of the needle tip portion 54 from the distal end opening 26 of the catheter 20 and adjustment (to a predetermined amount) of the amount of protrusion.

Still further, the catheter 20 is formed of a material containing polyurethane, making it possible to facilitate shaping of the tapered portion 24 of the catheter 20. That is, in the manufacture of the catheter 20, the catheter 20 is pressed against a heated mold and processed into a desired shape, and thereafter, the catheter 20 is covered with a tubular material and heated to be formed into a shape that conform to the shape of the inner needle 50 or the blade surface 58 of the inner needle 50. This processing causes heat shrinkage in the catheter 20, making it possible to allow the tapered portion 24 to further correspond to the shape of the blade surface 58 and mold the catheter into a shape with substantially no step between the tapered distal end of the catheter 20 and the blade surface 58. The processing of the tapered portion 24 is not limited to the above-described method, and any method capable of processing into a desired shape such as heat melting, heating deformation, and machine cutting may be used. Furthermore, the tapered portion 24 may be finally molded by only heat melting or the like, or may be molded by only covering a tubular material to use thermal shrinkage.

The catheter assembly 10 according to the present embodiment is essentially configured as described above, and its function and effect will be described below.

Figure 5A:
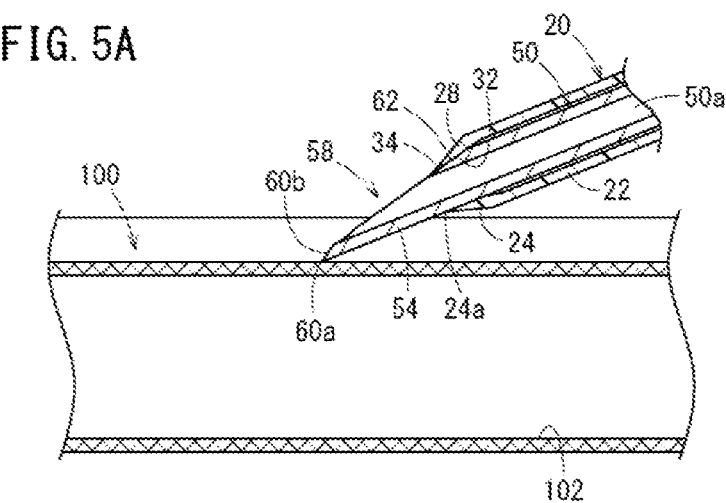
FIG. 5A is a first explanatory view illustrating operation at the time of puncture with the catheter assembly of FIG. 1.

As described above, the catheter assembly 10 is used, for example, in construction of an introduction part of infusion into a patient. In use of the catheter assembly 10, a user grasps the needle hub 70 and punctures the patient with the double structure needle 12 as illustrated in FIG. 5A. At this time, the point 60a and the ridge portion 60b of the needle tip portion 54 (pair of distal end split surfaces 60) exposed from the distal end of the catheter 20 first cut through the living tissue (skin, subcutaneous tissue, blood vessel wall, or the like) so as to insert the needle tip portion 54 into a blood vessel 100.

Figure 5B:
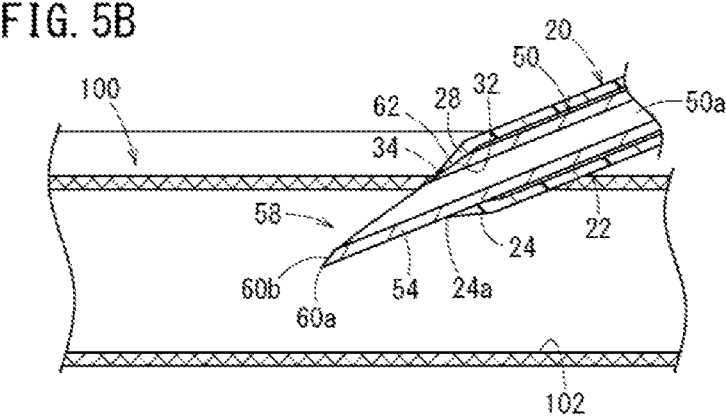
FIG. 5B is a second explanatory diagram illustrating operation at the time of puncture following FIG. 5A.

As illustrated in FIG. 5B, with the entry of the pair of distal end split surfaces 60 into the living tissue to advance the inner needle 50, the proximal end inclined surface 62 is next inserted into the living tissue, and then, the catheter 20 is also inserted into the living tissue. As described above, because the distal-most end 24a of the tapered portion 24 is in contact with the outer peripheral surface of the needle tip portion 54, suppressing occurrence of a step between the catheter 20 and the inner needle 50. This suppress resistance applied to the catheter 20 from the living tissue, leading to smooth insertion of the catheter 20.

In particular, the catheter assembly 10 has the proximal end inclined surface 62 of the needle tip portion 54 and the opposing surface 32 of the catheter 20 formed in a same shape and in contact with each other. Therefore, when a force in an advancing direction is applied to the double structure needle 12, the catheter 20 pressed against the living tissue forcefully comes into contact with the inner needle 50, suppressing misalignment or the like of the catheter 20 with respect to the inner needle 50. Furthermore, continuous connection at a large obtuse angle between the proximal end inclined surface 62 and the outer flat surface 34 facilitates movement of the living tissue from above the proximal end inclined surface 62 onto the outer flat surface 34, enabling smooth insertion of the tapered portion 24 into the blood vessel 100.

Figure 5C:
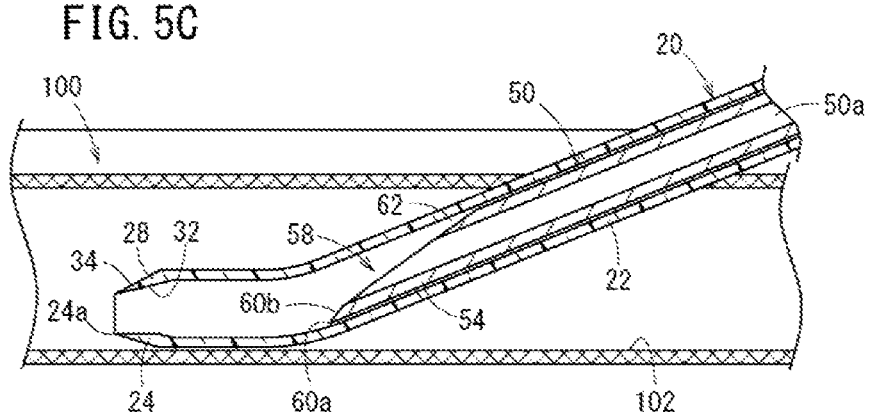
FIG. 5C is a third explanatory view illustrating operation at the time of puncture following FIG. 5B.

In addition, the catheter assembly 10 has a configuration in which the amount of protrusion of the needle tip portion 54 protruding from the distal end of the catheter 20 is small, making it possible to suppress an arrival of the needle tip portion 54 to a blood vessel inner wall 102 on an opposite side and therefore suppress damage caused by this when the tapered portion 24 is inserted into the blood vessel 100. Accordingly, as illustrated in FIG. 5C, the catheter 20 is advanced relative to the inner needle 50 after the catheter 20 is inserted into the blood vessel 100, enabling smooth insertion of the catheter 20 into the blood vessel 100.

After insertion of the catheter 20, the inner needle 50 is retracted relative to the catheter 20 in the proximal direction, so as to extract the inner needle 50 from the catheter 20. This allows the catheter 20 to be held in place satisfactorily in the blood vessel 100, and thereafter, the infusion tube is connected to the catheter hub 40. In the infusion, the catheter 20 can vigorously eject the infusion agent from the distal end opening 26 using the tapering tapered portion 24.

As described above, the catheter assembly 10 is configured such that the amount of protrusion of the inner needle 50 protruding from the distal-most end 24a of the tapered portion 24 is reduced due to the tapered portion 24 covering the proximal end inclined surface 62, making it possible suppress an influence (damage, etc.) to the blood vessel inner wall 102 at the time of puncture. In addition, the inner shape of the distal-most end 24a of the tapered portion 24 conforms to the blade surface 58, suppressing formation of a step between the catheter 20 and the blade surface 58, leading to reduction of resistance applied to the catheter 20 when the catheter 20 enters the living tissue. This enables the user to insert the catheter 20 smoothly into the living body.

In this case, with the distal-most end 24a of the tapered portion 24 being in contact with the outer peripheral surface of the inner needle 50 including the blade surface 58 (proximal end inclined surface 62), it is possible to further reliably suppress formation of the step between the catheter 20 and the blade surface 58. Note that the catheter assembly 10 can sufficiently suppress formation of a step provided that the inner shape of the distal-most end 24a of the tapered portion 24 conforms to the blade surface 58 even when the distal-most end 24a is somewhat separated from the blade surface 58. Furthermore, the tapered portion 24 is more easily subjected to the force in the advancing direction from the blade surface 58 of the inner needle 50 at the time of puncture, enabling the catheter 20 to be inserted more satisfactorily.

In addition, with the outer flat surface 34 provided on the tapered portion 24, it is possible to form the outer shape of the double structure needle 12 (catheter 20) that matches the blade surface 58. With this configuration, it is possible to achieve smooth transition from the blade surface 58 to the tapered portion 24 when the catheter 20 is inserted into the living body. Moreover, the intersecting angle X3 between the opposing surface 32 and the outer flat surface 34 is smaller than the inclination angle Y2 of the proximal end inclined surface 62, making it possible to sufficiently widen the obtuse angle at a boundary portion between the outer flat surface 34 and the blade surface 58. Accordingly, it is possible to achieve further smooth transition from the blade surface 58 to the tapered portion 24 when the catheter 20 is inserted into the living body.

Note that the catheter assembly 10 is not limited to the above-described configuration, and various configurations may be adopted. For example, the tapered portion 24 of the catheter 20 may have a configuration in which only the distal-most end 24a comes in contact with the outer peripheral surface of the inner needle 50, and the inner surface on more toward the proximal side than the distal-most end 24a is separated from the outer peripheral surface of the inner needle 50. In addition, the tapered portion 24 may have an outer peripheral surface formed in a conical shape, without having the outer flat surface 34.

Several modifications of the catheter assembly 10 will be described below. In the following description, the same reference numerals are given to components having the same configuration or the same functions as those of the catheter assembly 10 according to the present embodiment, and a detailed description thereof will be omitted.

First Modification

Figure 7A:
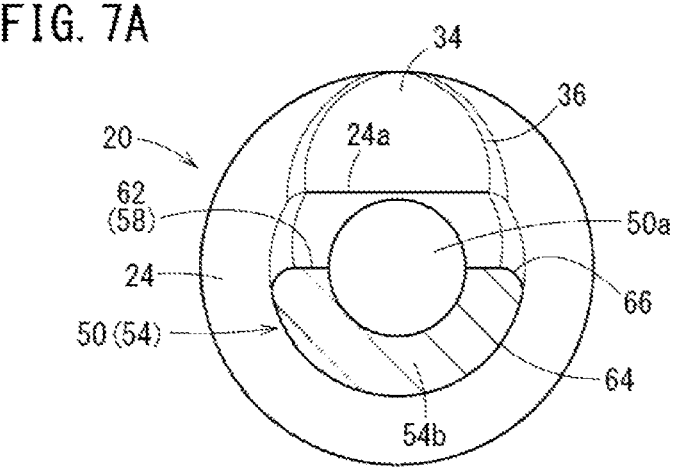
FIG. 7A is a cross section taken along line VIIA-VIIA of FIG. 6.
Figure 7B:
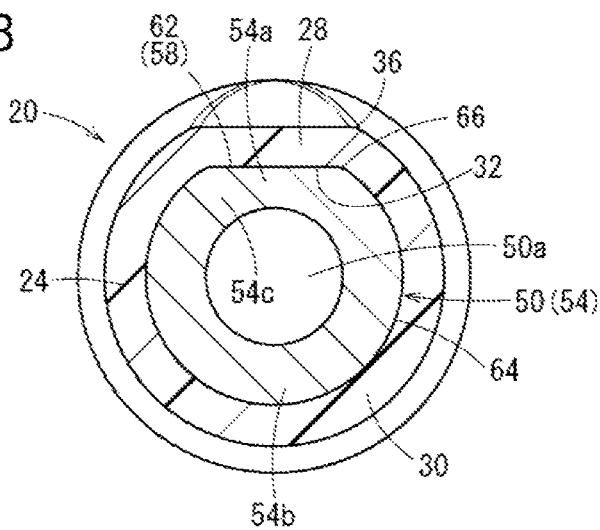
FIG. 7B is a cross section taken along line VIIB-VIIB of FIG. 6.
Figure 7C:
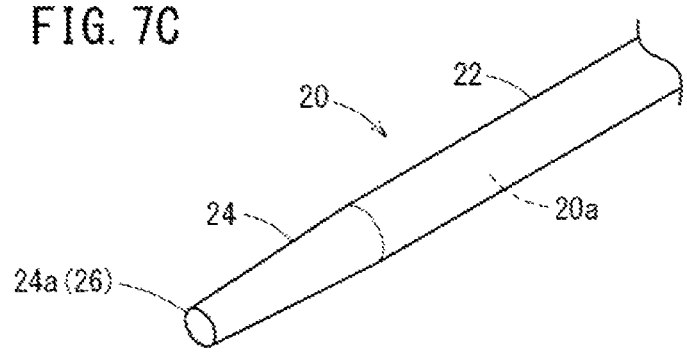
FIG. 7C is a perspective view illustrating a distal side of a catheter applicable to the double structure needle in FIG. 6.

As illustrated in FIGS. 6 to 7C, a double structure needle 14 according to a first modification is slightly different from the double structure needle 12 according to the present embodiment in shapes of the tapered portion 24 of the catheter 20 and the needle tip portion 54 of the inner needle 50.

Specifically, the needle tip portion 54 of the inner needle 50 includes a rounded corner wall portion 54c at a portion joining both side edges in the width direction of the inclined wall portion 54a and both side edges in the width direction of the arcuate wall portion 54b in the circumferential direction, in a cross section orthogonal to the center axis of the inner needle 50. The outer peripheral surface of the pair of rounded corner wall portions 54c is formed into a rounded corner surface 66 having a larger curvature than the arcuate surface 64. With a configuration with no corners connecting the proximal end inclined surface 62 and the arcuate surface 64, it is possible to reduce damage on the living tissue at puncture and facilitate insertion of the inner needle 50 into the living tissue.

The tapered portion 24 of the catheter 20 is configured to arrange each of the flat portion 28, the arcuate portion 30, and a rounded corner portion 36 respectively at a position in phase in the circumferential direction with each of the inclined wall portion 54a, the arcuate wall portion 54b, and the pair of rounded corner wall portions 54c, on the needle tip portion 54. The inner surface of the rounded corner portion 36 of the tapered portion 24 is formed into a curved surface that corresponds to the pair of rounded corner surfaces 66 of the inner needle 50. This configuration enables the tapered portion 24 to come in close contact, without any gap, with the proximal end inclined surface 62, the arcuate surface 64, and the pair of rounded corner surfaces 66 of the needle tip portion 54. In other words, the tapered portion 24 makes a surface contact with the outer peripheral surface of the needle tip portion 54, with the distal-most end 24a of the tapered portion 24 being substantially steplessly in contact with the circumferential direction of the needle tip portion 54 similarly to the above-described double structure needle 12.

As described above, with the catheter assembly 10 according to the first modification, it is possible to achieve similar effects as in the catheter assembly 10. That is, with the configuration in which each of the flat portion 28, the arcuate portion 30, and the rounded corner portion 36 of the tapered portion 24 respectively matches each of the blade surface 58, the arcuate surface 64, and the rounded corner surface 66, it is possible to allow the distal-most end 24a of the tapered portion 24 to be brought into contact with the outer peripheral surface of the inner needle 50 even when the inner needle 50 includes the rounded corner surface 66. In particular, the flat portion 28, the arcuate portion 30, and the rounded corner portion 36 are preliminarily shaped in a state where the inner needle 50 is not inserted through the catheter 20. This allows the catheter 20 and the inner needle 50 to come in close contact with each other more easily.

Note that the catheter 20 may be molded of a material having flexibility, with no preliminary shaping. That is, as illustrated in FIG. 7C, the catheter 20 may be configured to include the cylindrical outer needle side barrel 22 and the conical tapered portion 24 at the distal end of the outer needle side barrel 22 in a non-inserted state where the inner needle 50 is not inserted through the inner cavity 20a. In this case, the tapered portion 24 is brought into contact with the outer peripheral surface (the proximal end inclined surface 62, the arcuate surface 64, and the rounded corner surface 66) of the inner needle 50 in the assembled state, thereby deforming the shape of the tapered portion 24 so as to form each of the flat portion 28, the arcuate portion 30 and the rounded corner portion 36. At this time, because the inner needle 50 has the rounded corner surface 66, the conical tapered portion 24 can easily along to the rounded corner surface 66 as compared with an acute angled corner portion. That is, the flat portion 28 and the rounded corner portion 36 are easily formed along the outer peripheral surface of the inner needle 50, making it possible to suppress formation of a step with respect to the inner needle 50.

Second Modification

Figure 8:
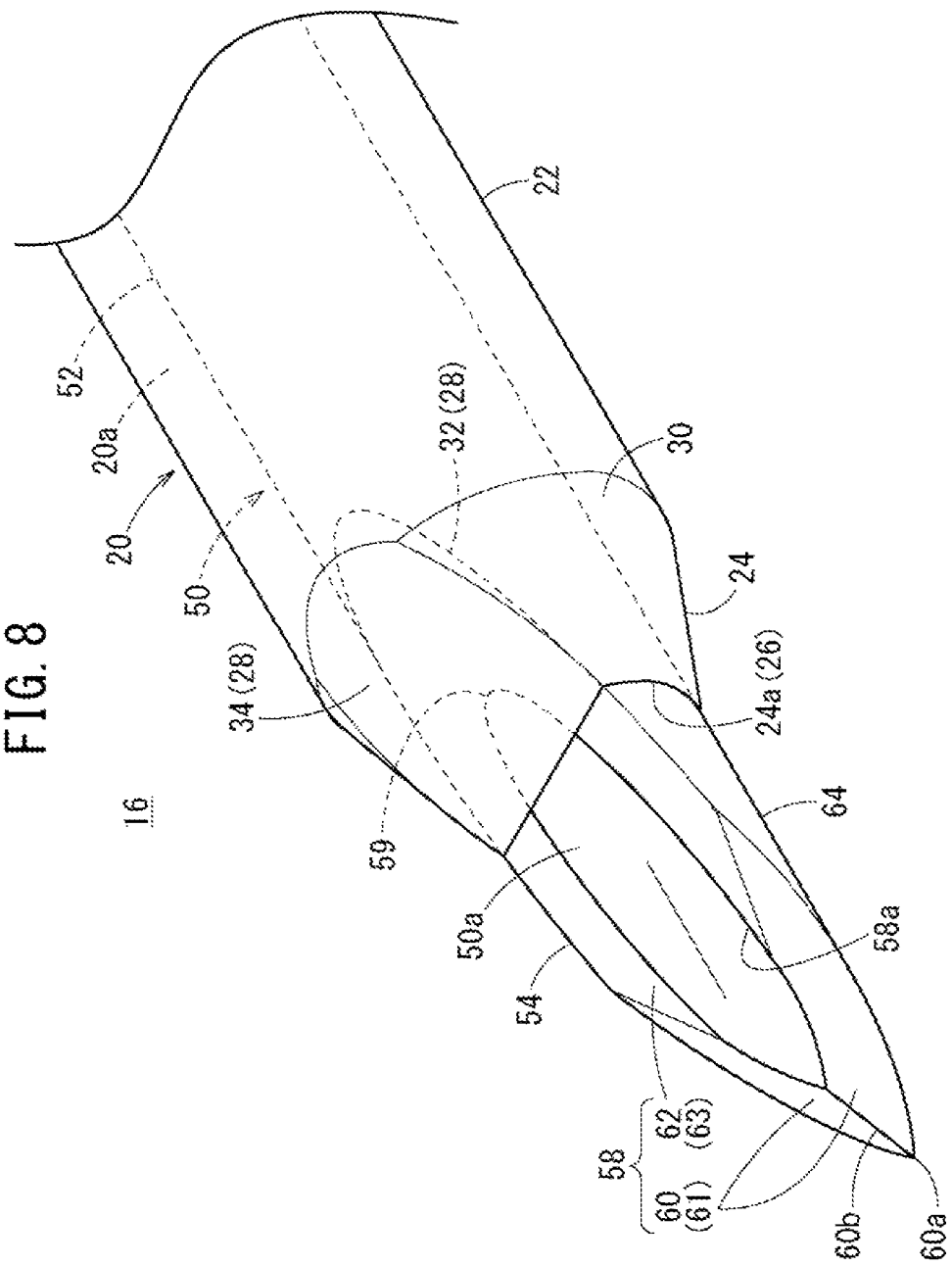
FIG. 8 is an enlarged perspective view illustrating a distal side of a double structure needle according to a second modification.

A double structure needle 16 according to a second modification illustrated in FIG. 8 has a configuration in which the tapered portion 24 of the catheter 20 partially covers the needle tip opening 58a of the inner needle 50. That is, the distal-most end 24a of the tapered portion 24 is disposed more toward the distal end of the needle tip portion 54 than the distal-most end 24a of the tapered portion 24 of the double structure needles 12 or 14, leading to reduction in the amount of protrusion of the needle tip portion 54. This configuration makes it possible to insert the catheter 20 into the blood vessel 100 immediately after puncturing the blood vessel 100 with the needle tip portion 54, making it possible to effectively suppress damage on the blood vessel inner wall 102 caused by the needle tip portion 54.

Furthermore, the flat portion 28 of the tapered portion 24 has its distal-most end 24a located on more toward the distal end than in the above-described double structure needle 12 or 14, and thus, is formed to be wider in the width direction corresponding to the blade surface 58 (proximal end inclined surface 62) of the inner needle 50. Similarly, to the catheter assembly 10, the intersecting angle X3 between the opposing surface 32 and the outer flat surface 34 is reduced. This enables the living tissue to smoothly slide on the outer flat surface 34 from the proximal end inclined surface 62 at the time of entry of the needle tip portion 54 into the living tissue. This makes it possible to reduce the resistance at insertion of the catheter 20.

Here, a lip 59 on the proximal side of the needle tip opening 58a forms curvature on the major axis side of the needle tip opening 58a, thereby forming a sharp edge with the needle hole 50a. Therefore, the lip 59 on the proximal side might hurt (damage) a living tissue if the lip 59 comes in contact with the living tissue at the time of puncture with the needle tip portion 54. In contrast, the double structure needle 16 according to the second modification has a configuration in which the tapered portion 24 covers the lip 59 on the proximal side of the needle tip opening 58a, making it possible to suppress the damage of the living tissue to be caused by the lip 59 on the proximal side of needle tip opening 58a.

Reference Example

Figure 9:
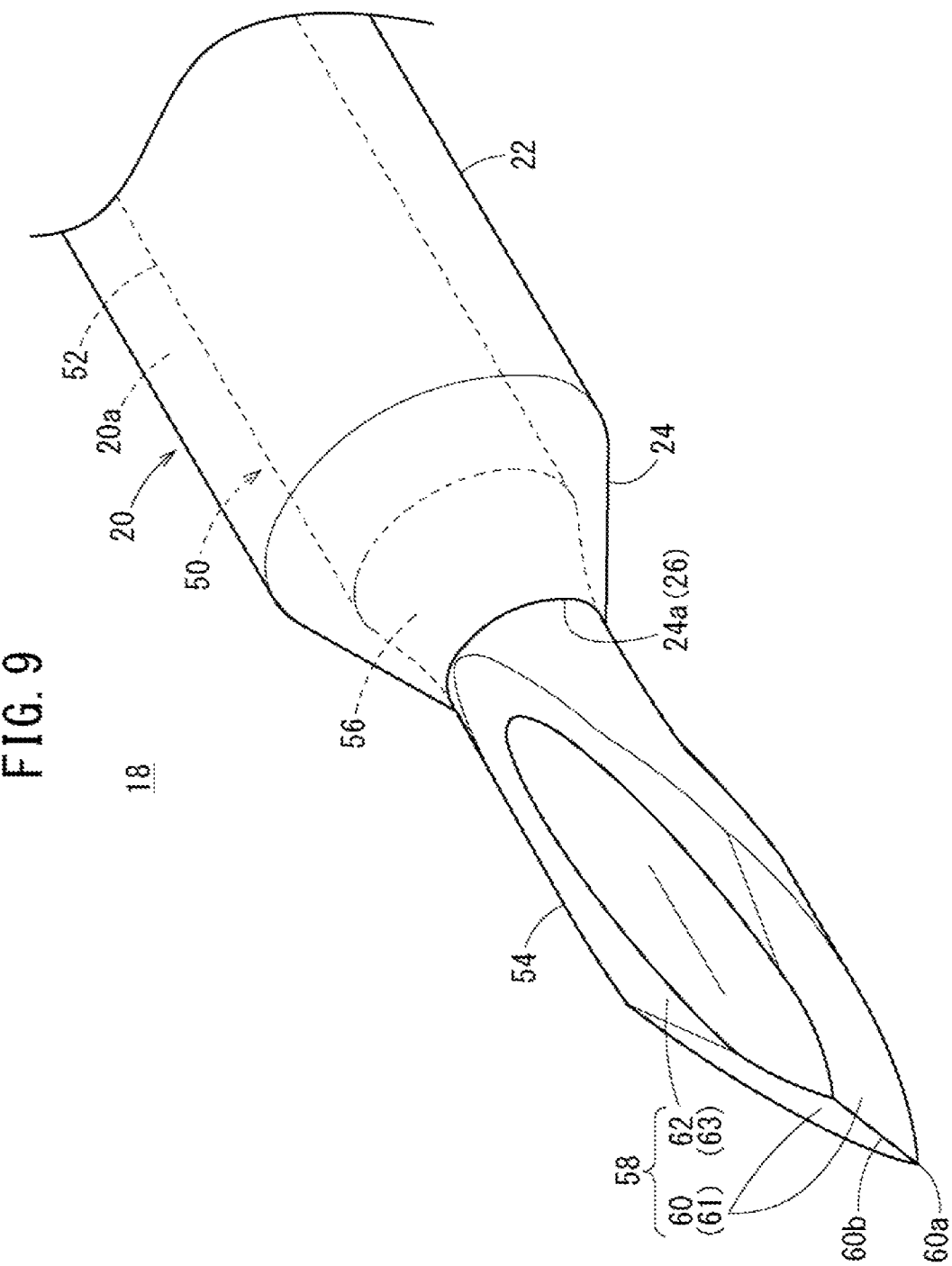
FIG. 9 is an enlarged perspective view illustrating a distal side of a double structure needle according to a reference example.
Figure 10:
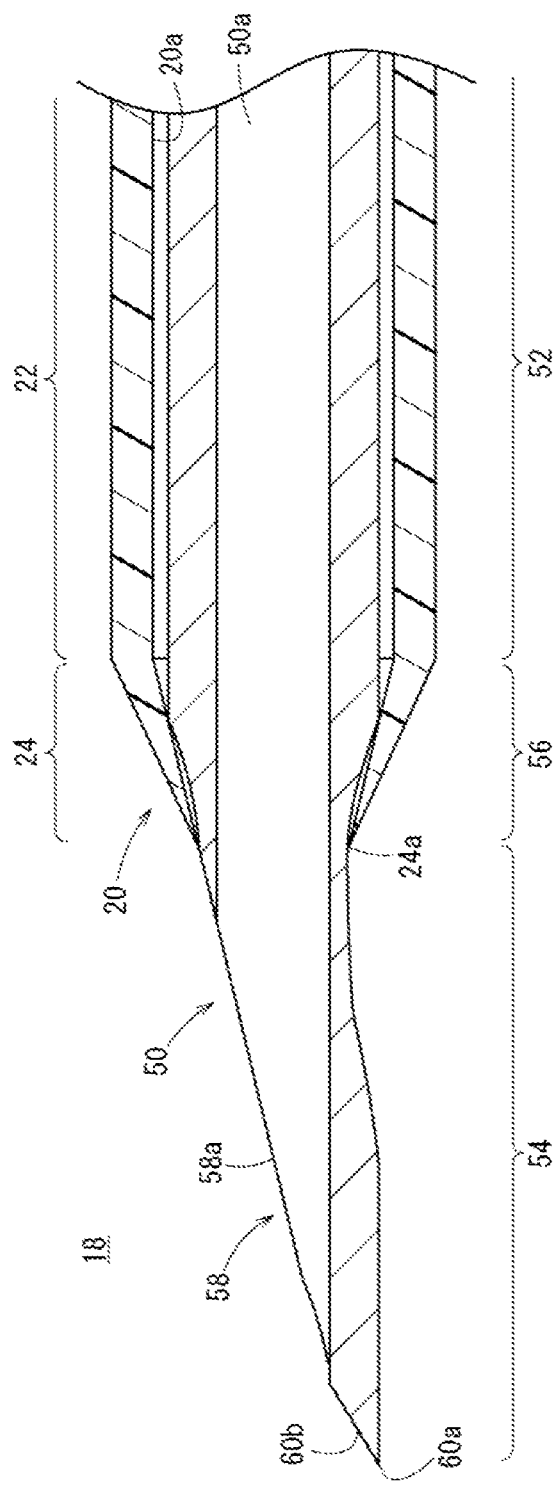
FIG. 10 is a side cross section of the double structure needle in FIG. 9.

As illustrated in FIGS. 9 and 10, a double structure needle 18 according to a reference example is different from the other double structure needles 12, 14, and 16 in that it includes a tapered transition portion 56 provided between the inner needle side barrel 52 and the needle tip portion 54 of the inner needle 50 and that the tapered portion 24 of the catheter 20 covers the transition portion 56.

Here, the catheter assembly 10 has settings with respect to the axial direction length of the blade surface 58 (needle tip portion 54) that is to be diagonally cut in normal cases, so as to be within a certain range in accordance with the thickness (outer diameter) of the outer needle side barrel 22. In contrast, with the transition portion 56 having a small diameter toward the distal direction, it is possible to gradually reduce the diameter of the outer diameter of the inner needle 50 on the distal side, enabling the reduction of the axial direction length of the blade surface 58 (needle tip portion 54) formed at the distal end of the transition portion 56. Therefore, the amount of protrusion of the inner needle 50 can be reduced simply by covering the transition portion 56 on the proximal side of the blade surface 58 with the tapered portion 24 of the catheter 20 in an initial state.

Meanwhile, in order to form a cut that enables smooth insertion of the catheter 20, the blade surface 58 is preferably formed to spread outward in the width direction (or vertical direction) from the distal end of the transition portion 56 toward the distal direction. This provides the inner needle 50 with a necked portion at a boundary between the transition portion 56 and the needle tip portion 54, making it easier to achieve contact of the distal-most end 24a of the tapered portion 24 in the circumferential direction.

Furthermore, with a configuration in which the tapered portion 24 of the catheter 20 does not cover the blade surface 58 (proximal end inclined surface 62), it is possible to form the tapered portion 24 in a conical shape corresponding to the inclination angle of the transition portion 56. That is, the tapered portion 24 may omit the flat portion 28 (the opposing surface 32 or the outer flat surface 34), facilitating the molding of the catheter 20. The distal-most end 24a of the tapered portion 24 may be in contact with a midway position of the transition portion 56 (on an outer peripheral surface of the transition portion 56) as well as being in contact with the boundary between the needle tip portion 54 and the transition portion 56. It is also allowable, of course, that the tapered portion 24 of the catheter 20 partially covers the blade surface 58 of the inner needle 50 even when the inner needle 50 includes the transition portion 56.

As described above, it is possible to reduce the amount of protrusion of the inner needle 50 protruding from the distal end of the catheter 20 even with the double structure needle 18 according to the reference example. This would result in suppression of damages on the blood vessel inner wall 102 caused by the inner needle 50 at the time of puncture with the double structure needle 18, leading to achievement of smooth insertion of the catheter 20 into the blood vessel 100.

The present invention is not limited to the above-described embodiment, and various modifications are possible without departing from the scope and spirit of the present invention as a matter of course.

What is claimed is:

1. A catheter assembly comprising:
a catheter having an inner cavity extending along a center axis of the catheter, the catheter comprising, on a distal side, a tapered portion that is tapered in a distal direction; and
an inner needle retractably located in the inner cavity;
wherein the inner needle comprises, on a distal side, a blade surface that is inclined with respect to a center axis of the inner needle;
wherein the tapered portion covers a proximal end portion of the blade surface in an assembled state in which the inner needle is located in the inner cavity, and an inner shape of a distal-most end of the tapered portion conforms to the blade surface;
wherein, in a cross section orthogonal to the center axis of the inner needle, an outer peripheral surface of the distal side of the inner needle comprises:
the blade surface, and
an arcuate surface; and
wherein in a cross section orthogonal to the center axis of the catheter in the assembled state, the tapered portion comprises:
a flat portion having an inner surface opposing the blade surface, and
an arcuate portion opposing the arcuate surface.

2. The catheter assembly according to claim 1, wherein the distal-most end of the tapered portion is in contact with the outer peripheral surface of the inner needle, including at the blade surface.

3. The catheter assembly according to claim 1, wherein the tapered portion comprises:
an outer flat surface on an outer surface side that corresponds to a circumferential position of the inner surface.

4. The catheter assembly according to claim 3, wherein an inclination angle of the outer flat surface with respect to the blade surface is smaller than an inclination angle of a proximal side portion of the blade surface with respect to the center axis of the inner needle.

5. The catheter assembly according to claim 3, wherein:
in the cross section orthogonal to the center axis of the inner needle, the outer peripheral surface of the distal side of the inner needle comprises:
a rounded corner surface joining the blade surface with the arcuate surface, the rounded corner surface having a larger curvature than the arcuate surface; and
in the cross section orthogonal to the center axis of the catheter in the assembled state, the tapered portion comprises:
a rounded corner portion joining the flat portion with the arcuate portion, the rounded corner portion opposing the rounded corner surface.

6. The catheter assembly according to claim 1, wherein:
the inner needle has a needle hole extending along the center axis of the inner needle, and the blade surface includes a needle tip opening communicating with the needle hole; and
the tapered portion covers a proximal end portion of the needle tip opening.

7. The catheter assembly according to claim 1, wherein:
the blade surface includes a first area having a distal end configured to form a cut, and a second area that is continuous with a proximal end of the first area and is configured to widen the cut; and the tapered portion partially covers the second area without covering the first area in the assembled state.

8. The catheter assembly according to claim 1,
wherein the catheter is formed of a material comprising polyurethane.

9. A method of making a catheter assembly comprising:
providing a catheter having an inner cavity extending along a center axis of the catheter, the catheter comprising, on a distal side, a tapered portion that is tapered in a distal direction; and
inserting an inner needle into the inner cavity;
wherein the inner needle comprises, on a distal side, a blade surface that is inclined with respect to a center axis of the inner needle;
wherein, after the inner needle is inserted into the inner cavity, the tapered portion covers a proximal end portion of the blade surface in an assembled state in which the inner needle is located in the inner cavity, and an inner shape of a distal-most end of the tapered portion conforms to the blade surface; and
wherein, in a cross section orthogonal to the center axis of the inner needle, an outer peripheral surface of the distal side of the inner needle comprises:
the blade surface, and
an arcuate surface; and
wherein in a cross section orthogonal to the center axis of the catheter in the assembled state, the tapered portion comprises:
a flat portion having an inner surface opposing the blade surface, and
an arcuate portion opposing the arcuate surface.

10. The method according to claim 9, wherein the step of providing the catheter comprises, before inserting the inner needle into the catheter, heating the catheter to form the tapered portion.

11. The method according to claim 9,
wherein, after the inner needle is inserted into the inner cavity, the distal-most end of the tapered portion is in contact with the outer peripheral surface of the inner needle, including at the blade surface.

12. The method according to claim 9,
wherein the tapered portion comprises:
an outer flat surface on an outer surface side that corresponds to a circumferential position of the inner surface.

13. The method according to claim 12,
wherein an inclination angle of the outer flat surface with respect to the blade surface is smaller than an inclination angle of a proximal side portion of the blade surface with respect to the center axis of the inner needle.

14. The method according to claim 12, wherein:
in the cross section orthogonal to the center axis of the inner needle, the outer peripheral surface of the distal side of the inner needle comprises:
a rounded corner surface joining the blade surface with the arcuate surface, the rounded corner surface having a larger curvature than the arcuate surface; and
in the cross section orthogonal to the center axis of the catheter in the assembled state, the tapered portion comprises:
a rounded corner portion joining the flat portion with the arcuate portion, the rounded corner portion opposing the rounded corner surface.

15. The method according to claim 14,
wherein the step of providing the catheter comprises, before inserting the inner needle into the catheter, shaping the flat portion, the arcuate portion and the rounded corner portion.

16. The method according to claim 9, wherein:
the inner needle has a needle hole extending along the center axis of the inner needle, and the blade surface includes a needle tip opening communicating with the needle hole; and
the tapered portion covers a proximal end portion of the needle tip opening.

17. The method according to claim 9, wherein:
the blade surface includes a first area having a distal end configured to form a cut, and a second area that is continuous with a proximal end of the first area and is configured to widen the cut; and
the tapered portion partially covers the second area without covering the first area in the assembled state.

18. The method according to claim 9,
wherein the catheter is formed of a material comprising polyurethane.

* * * * *